(12) United States Patent
Schick et al.

(10) Patent No.: US 7,927,010 B2
(45) Date of Patent: Apr. 19, 2011

(54) DISPOSABLE, PRE-CALIBRATED, PRE-VALIDATED SENSORS FOR USE IN BIO-PROCESSING APPLICATIONS

(75) Inventors: Karl G. Schick, Madison, WI (US); David Uhen, Burlington, WI (US)

(73) Assignee: SenCal, LLC, Middleton, WI (US)

( * ) Notice: Subject to any disclaimer, the term of this patent is extended or adjusted under 35 U.S.C. 154(b) by 590 days.

(21) Appl. No.: 11/780,685

(22) Filed: Jul. 20, 2007

(65) Prior Publication Data

US 2009/0134882 A1     May 28, 2009

Related U.S. Application Data

(62) Division of application No. 11/294,296, filed on Dec. 5, 2005, now Pat. No. 7,857,506.

(51) Int. Cl.
*G01N 25/58*     (2006.01)
*G01N 27/00*     (2006.01)

(52) U.S. Cl. .......... 374/45; 374/147; 374/174; 324/439; 324/441; 73/335.05

(58) Field of Classification Search .................. 374/1, 3, 374/29, 43–45, 159, 163, 183–185, 141, 374/147–148, 100, 135; 73/23.1, 23.21, 73/23.25, 23.41, 25.03, 25.01, 225.05, 649, 73/658, 661; 422/82.01, 82.02; 324/693, 324/439, 441–444, 450; 702/50, 179, 130–136, 702/99, 85, 81; 235/375, 462.1
See application file for complete search history.

(56) References Cited

U.S. PATENT DOCUMENTS

| | | | |
|---|---|---|---|
| 3,447,070 A * | 5/1969 | Sand et al. ..................... 324/450 |
| 4,147,596 A | 4/1979 | Babolan et al. |
| 4,227,151 A | 10/1980 | Ellis et al. |
| 4,303,887 A * | 12/1981 | Hill et al. ...................... 324/441 |
| 4,513,248 A * | 4/1985 | Miller ........................... 324/439 |
| 4,740,755 A | 4/1988 | Ogawa |
| 5,231,867 A | 8/1993 | Serwatzky |
| 5,384,028 A | 1/1995 | Ito |
| 5,421,983 A | 6/1995 | Slack |
| 5,435,170 A * | 7/1995 | Voelker et al. ............... 73/53.05 |
| 5,455,513 A * | 10/1995 | Brown et al. ................. 324/445 |
| 5,686,309 A * | 11/1997 | Frank et al. .................... 436/66 |
| 5,821,399 A | 10/1998 | Zelin |
| 5,869,971 A * | 2/1999 | Sherman ....................... 324/439 |
| 6,173,600 B1 | 1/2001 | Harada et al. |

(Continued)

FOREIGN PATENT DOCUMENTS

DE     197 20 504 A1     11/1998

(Continued)

OTHER PUBLICATIONS

U.S. Appl. No. 11/294,296, filed Dec. 5, 2005, Schick.

(Continued)

*Primary Examiner* — Gail Verbitsky
(74) *Attorney, Agent, or Firm* — Cook Alex Ltd.

(57) ABSTRACT

Disposable, pre-sterilized, and pre-calibrated, pre-validated conductivity sensors are provided. These sensors are designed to store sensor-specific information, such as calibration and production information, in a non-volatile memory chip on the sensor. The sensors are calibrated using 0.100 molar potassium chloride (KCl) solutions at 25 degrees Celsius. These sensors may be utilize with in-line systems, closed fluid circuits, bioprocessing systems, or systems which require an aseptic environment while avoiding or reducing cleaning procedures and quality assurance variances.

7 Claims, 5 Drawing Sheets

U.S. PATENT DOCUMENTS

| | | | |
|---|---|---|---|
| 6,259,242 B1 * | 7/2001 | Graham et al. | 324/71.4 |
| 6,275,717 B1 | 8/2001 | Gross et al. | |
| 6,350,382 B1 | 2/2002 | Schick | |
| 6,404,204 B1 | 6/2002 | Farruggia et al. | |
| 6,426,629 B1 * | 7/2002 | Edgson et al. | 324/439 |
| 6,607,669 B2 | 8/2003 | Schick | |
| 6,614,212 B2 * | 9/2003 | Brugger et al. | 324/71.1 |
| 6,623,698 B2 | 9/2003 | Kuo | |
| 6,650,933 B1 | 11/2003 | Obabkov | |
| 6,664,793 B1 * | 12/2003 | Sampson et al. | 324/439 |
| 6,673,622 B1 * | 1/2004 | Jina | 436/69 |
| 6,683,464 B2 | 1/2004 | Park et al. | |
| 6,712,963 B2 | 3/2004 | Schick | |
| 6,799,883 B1 | 10/2004 | Urquhart et al. | |
| 6,812,709 B2 | 11/2004 | Wieland et al. | |
| 6,828,808 B2 | 12/2004 | Srinivasan et al. | |
| 6,834,258 B2 * | 12/2004 | Schulte et al. | 702/183 |
| 6,930,486 B2 | 8/2005 | Muscarella et al. | |
| 7,287,699 B2 * | 10/2007 | Liu | 235/462.15 |
| H002228 H * | 1/2009 | Eick et al. | 324/441 |
| 7,523,649 B2 | 4/2009 | Corey et al. | |
| 7,733,097 B2 * | 6/2010 | Schenkl et al. | 324/693 |
| 2003/0020494 A1 | 1/2003 | Desmier et al. | |
| 2003/0145646 A1 | 8/2003 | Henry et al. | |
| 2004/0014233 A1 | 1/2004 | Bannister et al. | |
| 2004/0017201 A1 * | 1/2004 | Brugger et al. | 324/444 |
| 2004/0155066 A1 | 8/2004 | Schick | |
| 2004/0170530 A1 | 9/2004 | Hefti et al. | |
| 2005/0145020 A1 | 7/2005 | Mathur et al. | |
| 2005/0189936 A1 | 9/2005 | Quackenbush et al. | |
| 2005/0255491 A1 | 11/2005 | Lee et al. | |
| 2006/0014212 A1 | 1/2006 | Benkovic et al. | |
| 2006/0042964 A1 | 3/2006 | Mansouri et al. | |
| 2009/0180513 A1 * | 7/2009 | Schick et al. | 374/44 |
| 2010/0021993 A1 * | 1/2010 | Wang et al. | 435/286.1 |

FOREIGN PATENT DOCUMENTS

| | | |
|---|---|---|
| EP | 654664 A2 | 5/1995 |
| JP | 59160746 A | 9/1984 |
| JP | 100198354 | 1/1998 |
| WO | WO 92/17775 | 10/1992 |
| WO | WO 00/06761 | 2/2000 |

OTHER PUBLICATIONS

U.S. Appl. No. 11/741,162, Apr. 27, 2007, Schick.
U.S. Appl. No. 12/407,553, filed Mar. 19, 2009, Schick.
PCT/US2006/061561 International Search Report and Written Opinion, dated Jun. 4, 2007.
"Siemens (unit)", Wikipedia, http://en.wikipedia.org/wiki/Siemens_(unit), Oct. 5, 2009, USA.

* cited by examiner

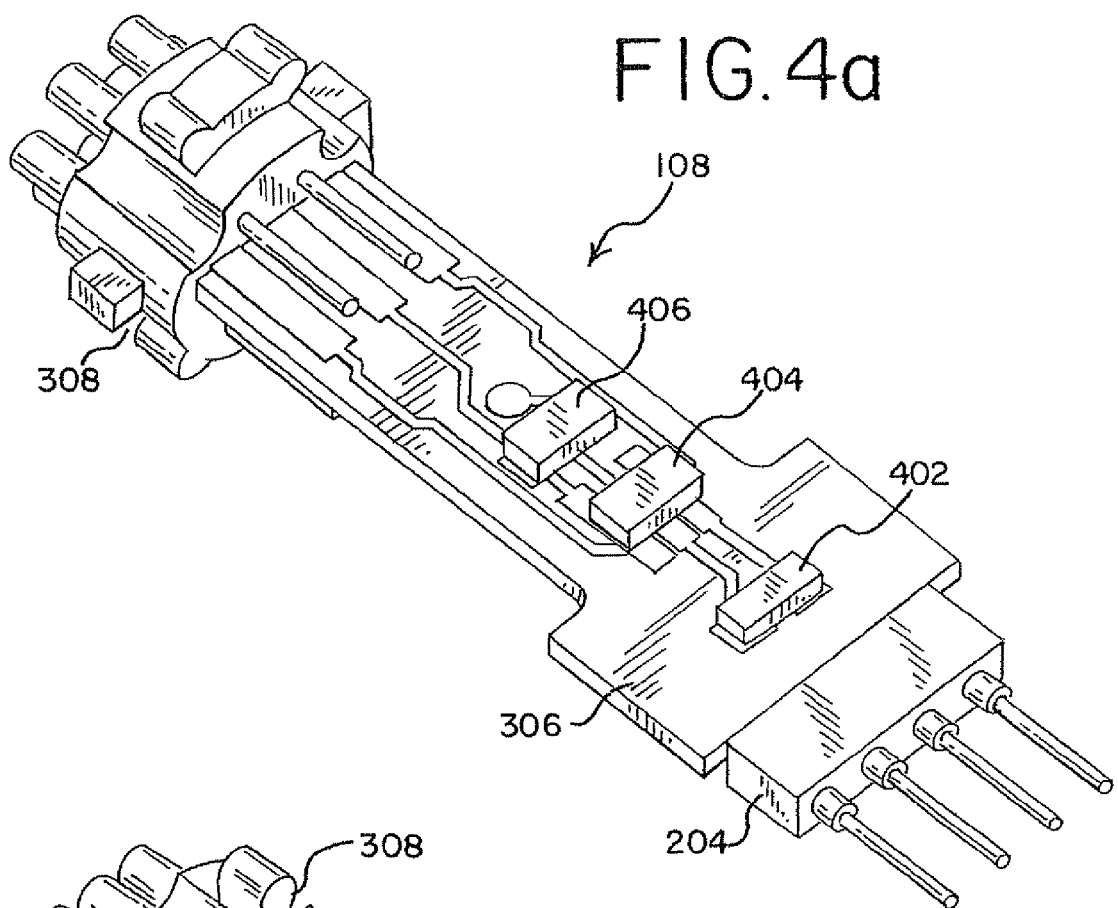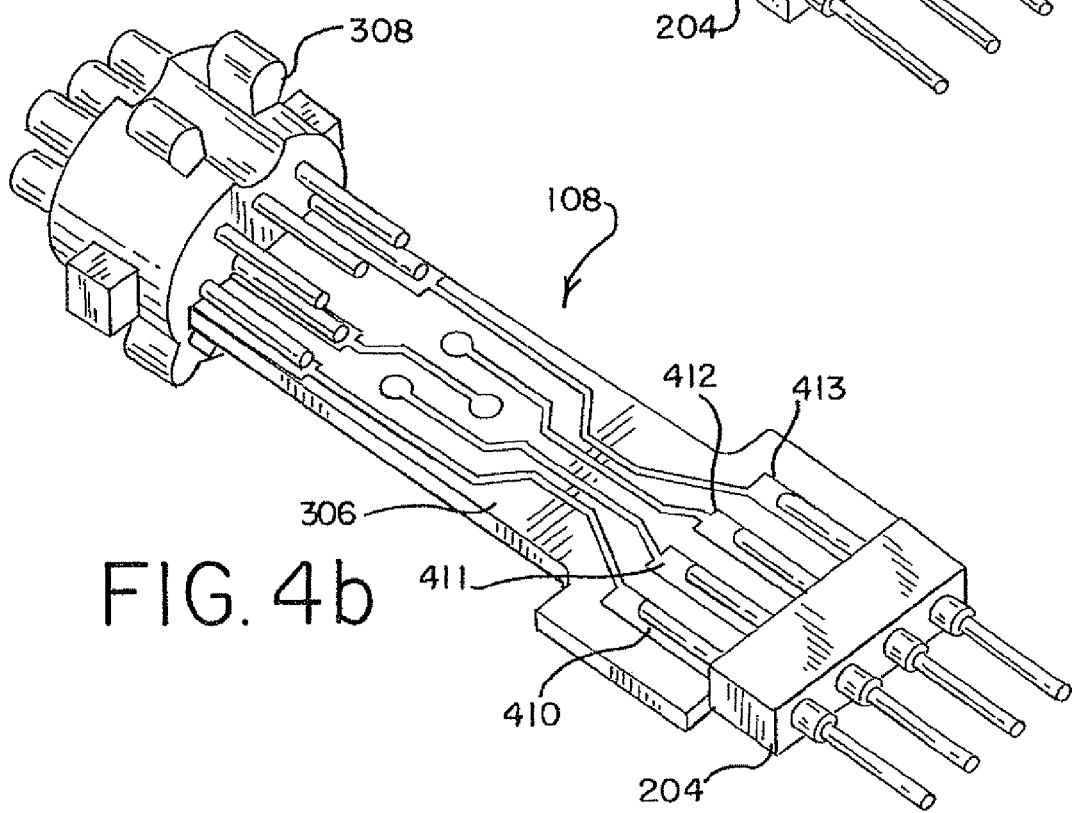

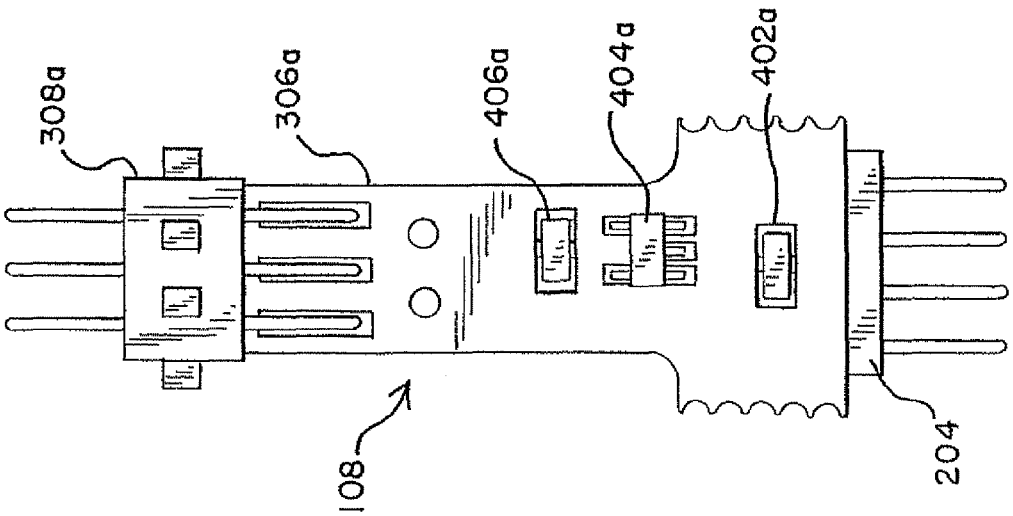
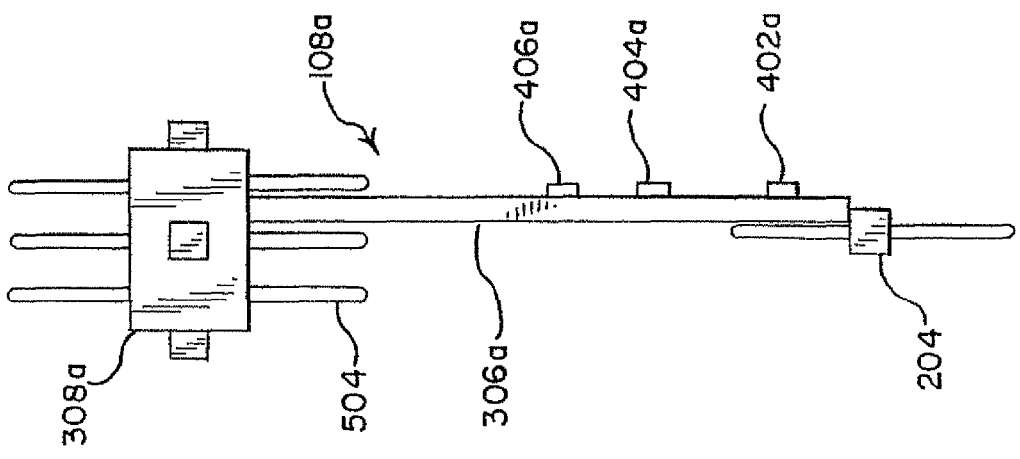
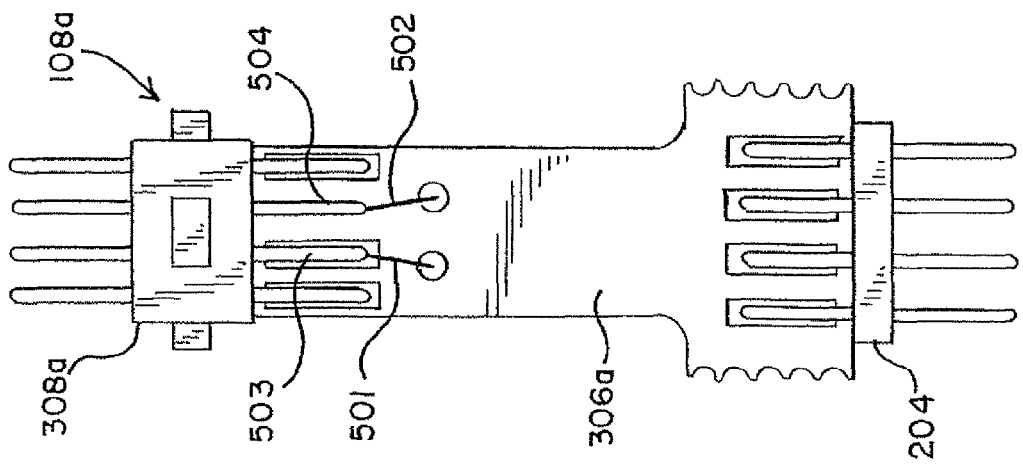

DISPOSABLE, PRE-CALIBRATED, PRE-VALIDATED SENSORS FOR USE IN BIO-PROCESSING APPLICATIONS

FIELD OF THE INVENTION

The invention generally relates to disposable, pre-sterilized, pre-calibrated, in-line sensors. More specifically, the invention relates to disposable, pre-calibrated, pre-validated probes or sensors that contain non-volatile memory capable of storing specific conductivity and preferably also information concerning the "out-of-box" performance of the probe or sensor.

BACKGROUND OF THE INVENTION

Pre-sterilized, single-use bag manifolds such as those used in bio-pharmaceutical production (see U.S. Pat. No. 6,712,963, incorporated here by reference) lack the ability to monitor and validate important, analytical solution parameters during the processing of biopharmaceutical solutions. The use of such bag manifolds, for example, in preparative chromatography or tangential flow filtration (TFF) or fluid transfer generally, is severely limited by the general lack of pre-sterilized, pre-calibrated, pre-validated in-line sensors and detectors In-line, flow through-type sensors and detectors are well known in industry and are extensively used in analytical laboratories, pilot plants and production facilities. In-line conductivity detectors, in particular, are used in ion chromatography, preparative chromatography, flow injection analysis (FIA), tangential flow filtration (TFF), as well as water purity analysis. However, prior-art in-line flow through conductivity sensors and detectors are typically made out of machined, stainless steel or plastic materials. These sensors and detectors are intended for permanent installations and long-term use. Prior-art in-line sensors and detectors are difficult to sterilize, require in-field calibration and validation by an experienced operator before use, and are very expensive, often costing thousands of dollars. Consequently, prior art sensors and detectors are not suited for a single-use sensor application.

The use of a memory device imbedded in disposable clinical sensors has been reported. For example, U.S. Pat. No. 5,384,028 deals with the fabrication of an enzyme-based glucose biosensor that utilizes a sensor-imbedded data memory device. However, this patent utilizes the memory device for purposes of sensor traceability and inventory control. Furthermore, this patent requires sensor calibration and/or validation by the clinician immediately prior to each use.

In line sensors for use in bioprocessing applications must be designed to meet government regulations regarding device traceability and validation. In addition, in-line sensors must meet the application requirements for accuracy and precision. These requirements present extra challenges and pose unique problems when the in-line sensor is to be disposable and suitable for single use as desired. Another problem is how to provide disposable in-line sensors that are pre-calibrated. Also for aseptic sensor applications, each single-use sensor, must meet sterilization requirements. Furthermore, single-use sensors must meet economic requirements, i.e. sensors must be low cost, easy to replace with negligible disposal expense.

SUMMARY OF THE INVENTION

The present invention overcomes the aforementioned shortcomings and problems faced by the industry by providing a low-cost, pre-sterilized, pre-calibrated, in-line sensor capable of being traced and validated. The invention further provides a sensor-embedded, non-volatile memory chip capable of storing device-specific information for instant recall by the user.

The preferred embodiment is an in-line conductivity sensor system used to measure the conductivity of the process flow solution. The present embodiment has two main components: the user interface and the sensor assembly module.

The sensor assembly module contains a short tubular fluid conduit, one or more sensor or probe components, referred to herein at times as a sensor or a sensor component. The sensor assembly module further includes a printed circuit board (PCB) with a sensor-embedded non-volatile memory chip. Sensor components can include electrodes, toroidal sensors or other arrangements. All components are designed or selected for highly automated production methods such as those used in surface mounted electronic assemblies. The present disclosure focuses on multiple electrode arrangements as the preferred embodiment for carrying out the sensing function.

In the illustrated preferred embodiment, four electrodes are press-fitted into and through four, linearly arranged holes in the fluid conduit wall. The electrodes are epoxied, cemented or sealed into place to prevent leaks or contamination. The electrodes are connected to a PCB. The PCB contains a thermistor, in thermal contact with two of the conductivity electrode pins. The PCB also contains a non-volatile memory chip or EEPROM, which is used to store sensor-specific information, which typically includes the sensor's ID number, a Cell Constant, a Temperature Offset Value and the calibration date.

Furthermore, each sensor has an "out-of-box" performance variance value which is also stored in the non-volatile memory chip. This "out-of-box" value is a statistically derived performance variance (measured for example in 0.100 molar KCl at 25.0° C.) that represents the maximum measurement error for that specific sensor within a 98% confidence limit. The statistically derived variance value is based on the performance analysis of all calibrated sensors within a production run, typically of between about 100 and about 500 sensors. The factory determined performance variance represents a predictive, "out-of-box" sensor performance level.

The user interface performs the conductivity measurement by monitoring the current across the two inner working electrodes. Prior to the conductivity measurement, the user interface retrieves the Cell Constant from the sensor memory. The measured solution conductance is multiplied by the Cell Constant to arrive at the actual conductivity of the tested process solution. The sensor-specific Cell Constant is determined during factory calibration using a solution (for example 0.100 molar KCl at 25.0° C.) with a known conductivity. The Cell Constant is subsequently stored in the non-volatile memory of the sensor assembly module.

It is a general aspect or object of the present invention to provide a disposable conductivity sensor.

Another aspect or object of the present invention is to provide a disposable sensor suitable for one-time use, which may be integrated with other disposable equipment, including bag manifolds, employed in the separation and purification of fluids, that are suitable for single-use applications.

An aspect or object of the present invention is to reduce the cost associated with the construction of conductivity sensors.

Another aspect or object of the present invention is to provide a sensor having a stored "out-of-box" performance variance value.

These and other objects, aspects, features, improvements and advantages of the present invention will be clearly understood through a consideration of the following detailed description.

BRIEF DESCRIPTION OF THE DRAWINGS

FIG. 4a is a perspective view of the component side of the illustrated conductivity sensor;

FIG. 4b is a perspective view of the underside of the illustrated conductivity sensor;

FIG. 5a is a plan view of the underside of another embodiment of a conductivity sensor;

FIG. 5b is an elevation view of the conductivity sensor of FIG. 5a; FIG. 5c is a plan view of the component side of the conductivity sensor of FIG. 5a.

DETAILED DESCRIPTION OF THE EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

Figure 1:
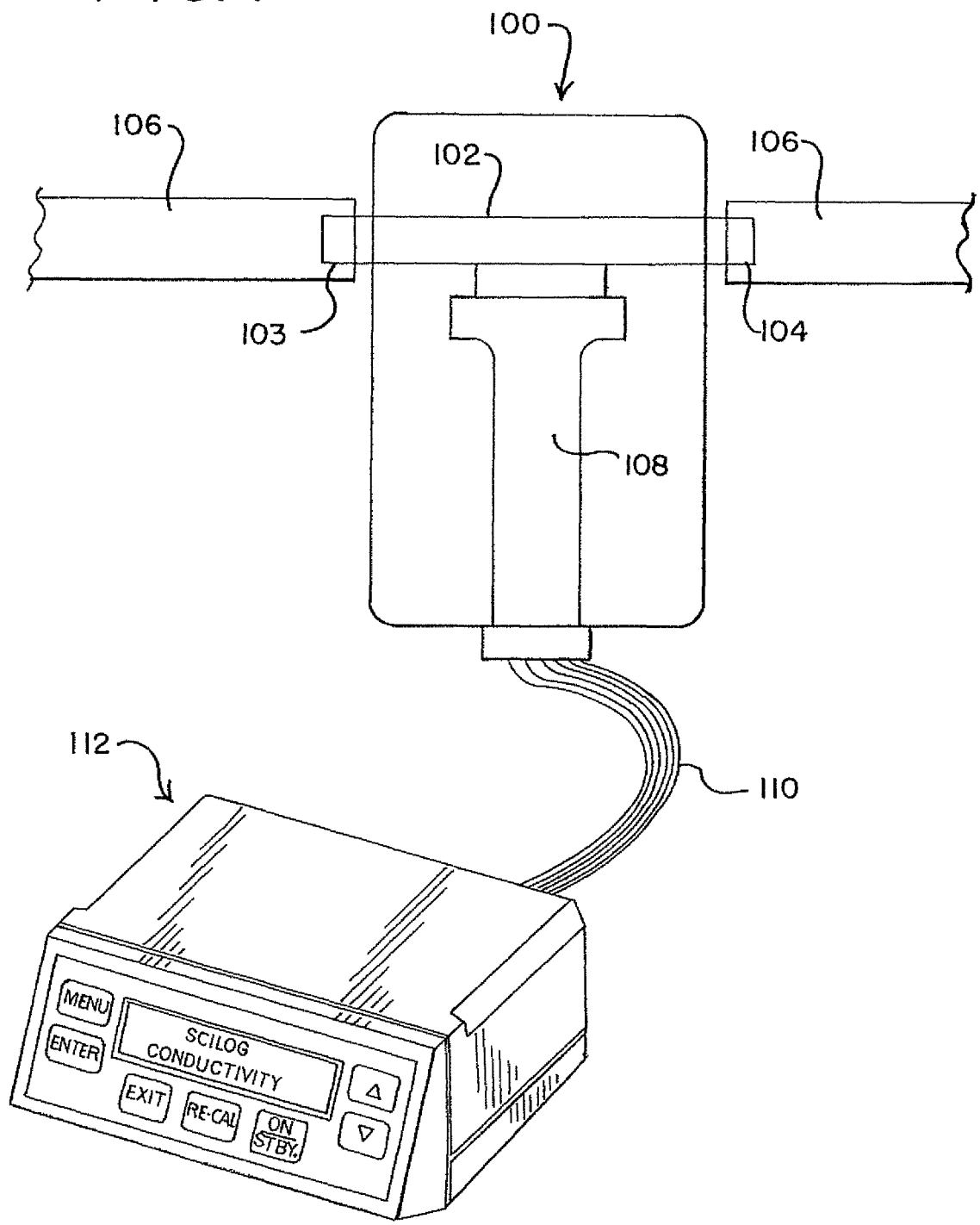
FIG. 1 is an illustration of a preferred embodiment of the user interface and of the conductivity sensor assembly that is attached at both ends of a fluid conduit of a fluid transfer system.

A system designed to measure the conductivity of fluids in a closed fluid system by using a pre-calibrated disposable in-line electrical conductivity sensor is shown in FIG. 1. The electrical conductivity sensor assembly is generally designated as 100. The assembly 100 is designed to be integrable with a fluid circuit and to be disposable. Contained with the conductive sensor assembly 100 is a short tubular fluid conduit 102, designed for a particular manifold flow rate range of the fluid circuit. Typically, the fluid conduit 102 is tubular and has a diameter between about 3 mm and about 25 mm (about ⅛ inch and about 1 inch). The flow conduit 102 is made of a polymer such as a polyolefin, for example polypropylene, but any other appropriate plastic tubing or material may be substituted. The tubing material should be suitable for engaging and containing the fluid being handled, such as valuable proteins, biotechnical compositions or pharmaceutical solutions. The flow conduit 102 has molded-in fluid-tight connections 103 and 104, which may consist of Luer, Barb, Triclover, or any connection method suitable to connect the flow conduit 102 in a processing system or fluid circuit, such as the illustrated polymeric tubing 106. A sensing portion or conductivity sensor 108 protrudes through the wall of the conduit in a manner that will be more evident in the subsequent discussion and from the drawings.

Leads such as the illustrated electrical connecting wires 110 connect the conductivity sensor 108 to a conductivity readout device or user interface 112. The user interface, generally designated as 112, communicates with the sensor 108 and measures conductivity by sending and receiving both digital and analog electrical signals along the leads 110. The user interface 112 has a display 114 to display information, for example, the conductivity reading, the temperature reading, and information stored on the conductivity sensor 108 relating to the calibration, validation and tracking of the sensor.

Figure 2:
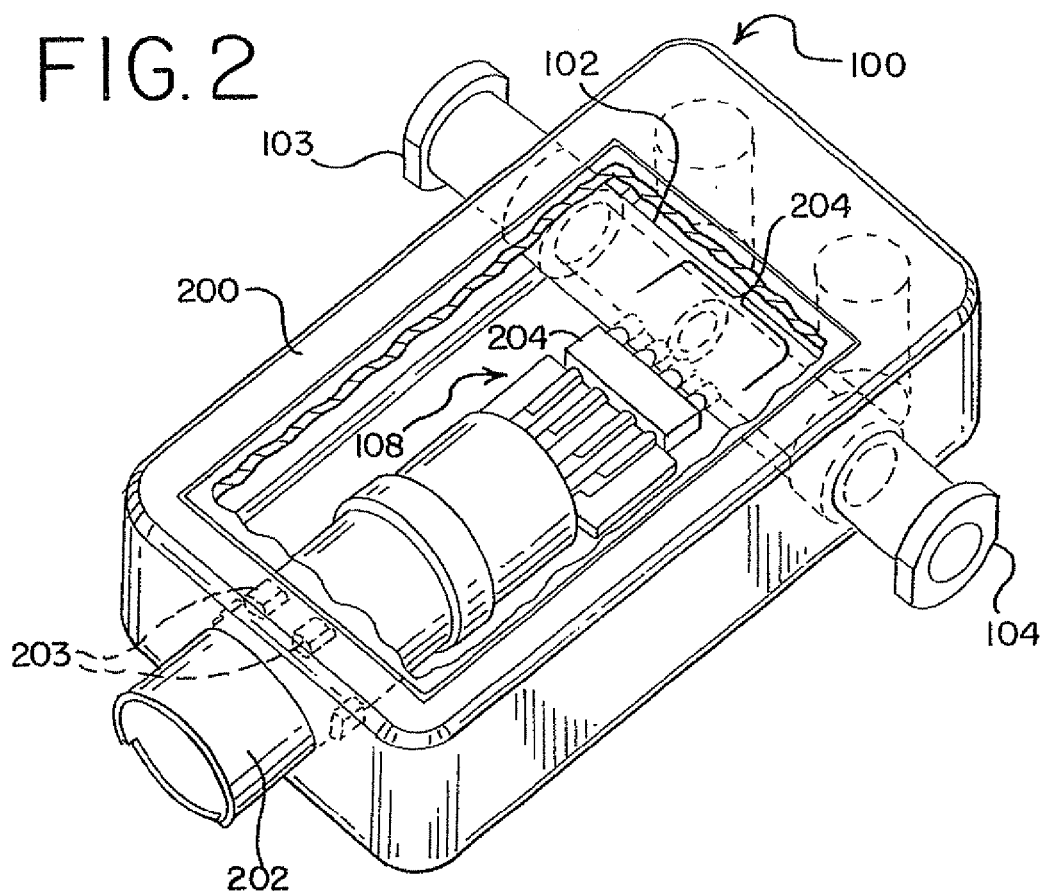
FIG. 2 is a cut-away perspective view of the illustrated conductivity sensor assembly.

FIG. 2 is a more detailed view of the conductivity sensor assembly 100. The housing 200 of the assembly 100 preferably is over-molded with a durable material such as a hard polyurethane polymer such as TPE. The durable housing material seals and protects the interior components from moisture and outside contaminants. The sensor 108 can be further protected by a sheath 202 as illustrated.

The fluid conduit 102 traverses the assembly 100 such as along its width as illustrated. Electrodes 204 are in electrical communication with the interior of the fluid conduit 102. In the illustrated embodiment, the fluid conduit is intersected by four electrodes of the conductivity sensor 108. These electrodes 204 can be positioned along the interior of the conduit 102, such as at the middle portion of the conduit. Gold-plated electrodes can be used such as ones that are about 1 mm to about 2 mm in diameter or between about 0.025 inches to 0.05 inches in diameter. Such electrodes preferably are arranged in-line approximately 2 to 2.5 mm (about 0.08 inch to 0.10 inch) apart.

In the illustrated embodiment, the electrode pins 204 are press-fitted into and through four linearly arranged holes in the wall of the fluid conduit 102 and extend into the hollow interior of the fluid conduit 102. Typical protrusion into the conduit is on the order of about 3 mm to about 13 mm (about ⅛ inch to about 0.5 inch). The electrodes 204 are epoxied, cemented or otherwise sealed to the wall of the fluid conduit 102 to prevent leaks or contamination. Additionally, the electrodes 204 are in electrical communication with their respective traces on the sensor 108.

In other embodiments, the electrodes 204 may only have two electrodes or pins rather than four of the preferred embodiment. In addition, the electrodes may be constructed from other materials, such as stainless steel wire, titanium wire, or any other non-corrosive material. Disposability is a criteria to be considered in selecting these or any other materials of the device.

Figure 3:
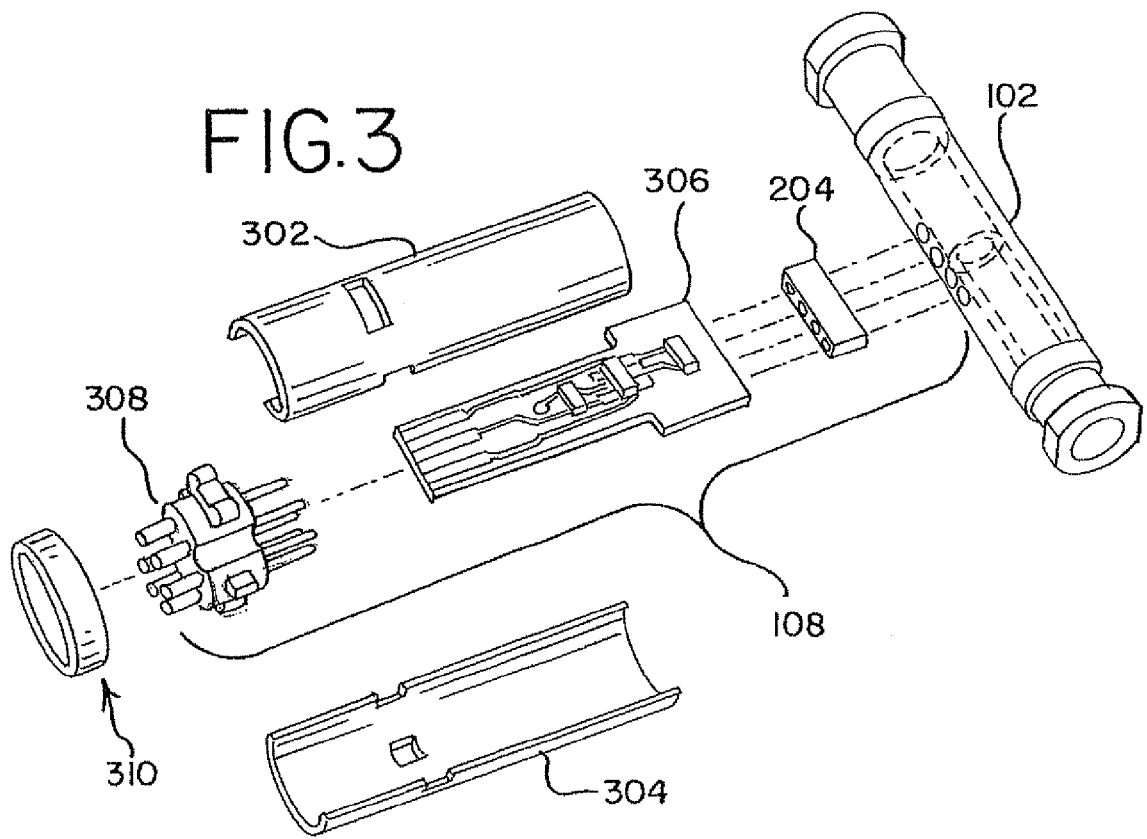
FIG. 3 is an exploded perspective view illustration of the illustrated conductivity sensor and the fluid conduit.

FIG. 3 shows a component view of the fluid conduit 102, sensor 108, and sheath 202. The illustrated sheath 202 has a top portion 302 and a bottom portion 304. The illustrated electrodes 204 are press-fitted into and through the wall of the fluid conduit 102 and are connected to the printed circuit board (PCB) 306 of the conductivity sensor 108. The preferred PCB 306 is a double sided PCB with conductive solder traces. Each pin of the electrodes 204 is in direct contact with its respective trace, and each is shown soldered onto the printed circuit board (PCB) 306.

Opposite the electrodes 204, the PCB 306 is wedged between two rows of five pins of a miniature, 8-pin DIN connector 308. These five pins of the DIN connector 308 are in direct contact with the PCB 306 and are soldered to the PCB 306. The three remaining pins of the DIN connector 308 are wired and soldered to the PCB 306. The end of the sensor 108 is capped and sealed by the cap-ring 310. The DIN connector 308 is detachably connected to the user interface 112 by the connecting wires 110. Each pin of the DIN connector 308 is associated with an individual wire of the connecting wires 110.

FIG. 4a shows the top view or the component view of the sensor 108. The electrodes 204 are connected to the underside of the PCB 306. A surface-mounted thermistor 402 is in thermal contact with two of the conductivity electrode pins when four are provided. A second, important function of the thermistor is to act as a pull-up resistor for the non-volatile memory chip, thereby assuring proper functioning of the memory device. The thermistor 402 is used to monitor the temperature of the solution in the fluid conduit 102, via thermal conductance, such being transmitted to the user interface 112. The user interface 112 reports the solution temperature data and utilizes the temperature data to correct or normalize the solution conductivity reading.

A sensor-embedded non-volatile memory chip or an EEPROM 404 is mounted on the surface of the PCB 304. The non-volatile memory chip or EEPROM 404 is used to store sensor-specific information. This information can be called up, displayed and printed out, on demand, by the user interface 112.

The PCB 306 also contains a surface-mounted capacitor 406 that is visible in FIG. 4a. FIG. 4b is an illustration of the underside of the PCB 306 in the four electrode embodiment. The electrodes 204 are soldered to their respective traces 410, 411, 412, and 413. FIG. 4b also further demonstrates the wedging of the PCB 306 between the pins of the DIN connector 308.

FIG. 5a is a plan view of the underside of a PCB 306a of the conductivity sensor 108a. Hand soldered connections 501 and 502 to the PCB connect two pins 503, 504 of the 8-pin DIN connector 30a that are not in direct contact.

FIG. 5b is an elevation view of the conductivity sensor 108a. FIG. 5b also shows how the PCB is sandwiched between the pins of the DIN connector. The low profiles of the capacitor 406a, non-volatile memory chip 404a and the thermistor 402a are also evident in FIG. 5b.

FIG. 5c is a plan view of the conductivity sensor 108a that is shown in FIG. 5a and FIG. 5b.

Figure 6:
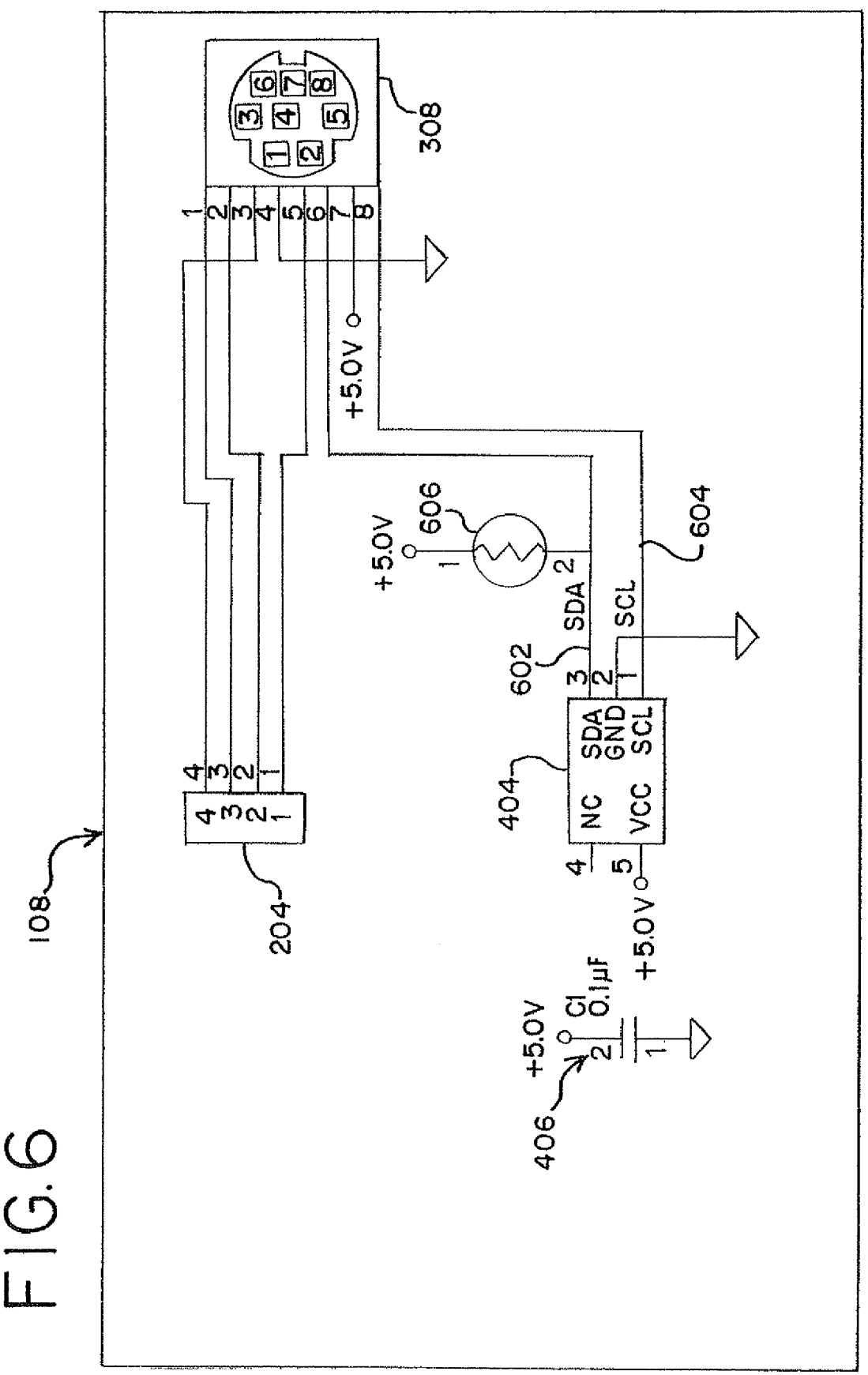
FIG. 6 is a schematic circuit diagram of the illustrated conductivity sensor.

FIG. 6 is an electric circuit diagram illustrating the various connections of the sensor 108 in the preferred embodiment that is illustrated. Four connections from the 8-Pin DIN connector 308 are connected to the four pins of the electrode 204. One pin of the DIN connector 308 provides a 5.0 Volt power supply to the capacitor 406, the non-volatile memory chip (or EEPROM) 404, and a bi-directional serial data line 602. One pin of the DIN connector 308 provides the ground for the capacitor 406 and the non-volatile memory chip (or EEPROM) 404.

The non-volatile memory chip (or EEPROM) 404 uses the bi-direction serial data line 602 and a serial clock line 604 to communicate with the user interface. Different non-volatile memory chips or EEPROMS have different protocols, which are known in the art. In this embodiment, the serial data and serial clock lines allow a user interface 112 or a calibration device to read, erase, and write data to the non-volatile memory chip 404. The serial data line 602 is an open drain terminal. Therefore, the serial data line requires a pull-up resistor 606 connected to the voltage source coming from the DIN connector 308. The in this embodiment, the thermistor 402 also serves as the pull-up resistor 606.

The sensor-specific information is electronically entered into the non-volatile memory chip 404 during factory calibration of the conductivity sensor 108. The sensor-specific information may include the following: Cell Constant (K), Temperature Offset, the unique Device ID, and the Calibration Date, the production lot number of the sensor, the production date of the sensor, the type of fluid used for calibration, the actual temperature of the fluid used, and "out-of-box" sensor performance value.

During production, small differentiations in the electrodes 104, the respective angles of the electrodes, and the gaps between the individual electrodes will result in different conductivity readings for each sensor produced. These differences can significantly affect accuracy. In keeping with the invention, these differences are successfully addressed by having each sensor normalized or calibrated as a part of its manufacturing procedure.

In the illustrated example, each conductivity sensor 108 is calibrated using certified 0.100 molar KCl (potassium chloride) solution maintained at 25.0° C. The conductance, which is dependent on the cell geometry and the solution resistivity, is determined by measuring the voltage drop across the electrodes. The measured conductance together with known solution conductivity allows the calculation of the sensor-specific Cell Constant (K). The Cell Constant (K) is determined by the following equation:

ti [Solution Conductivity,(S/cm)]/[Conductance (S)]=[Cell Constant, $K$,(cm$^{-1}$)]

The sensor-specific Cell Constant (K) is then stored in the non-volatile memory 404 of the conductivity sensor 108.

For example, the solution conductivity for a 0.100 molar KCl solution is known to be 12,850 µS (or 0.01285 S) at 25.0° C. The typical measured conductance for a 0.100 molar KCl solution using a sensor with a ⅛ inch Luer conductivity cell with a 0.10 inch electrode separation is 0.0379 Siemens. Using the equation above, the corresponding Cell Constant (K) for the particular disposable sensor of this illustration is calculated to be 0.339 cm$^{-1}$.

Once the Cell Constant (K) is calculated it is stored on the sensor. The user interface will recall the Cell Constant (K) from the sensor. When undergoing normal operations, the user interface 112 measures the conductance in Siemens of the solution flowing through the fluid conduit 102 by passing a current through the electrodes 204 and measuring the current across the two inner electrodes 204. The user interface 112 will then use the Cell Constant (K) for this particular disposable sensor to determine the conductivity of the solution flowing through the fluid conduit. The user interface calculates the solution's conductivity by multiplying the measured conductance by the Cell Constant (K), as demonstrated in the following equation:

[Cell Constant, $K$,(cm$^{-1}$)]×[Conductance (S)]=[Solution Conductivity,(S/cm)]

The sensor, once calibrated, provides a linear response for NIST traceable standard solutions ranging from 1 to 200,000 µS.

The temperature of a solution will also affect its conductivity. As a result, the sensor must also measure and account for the temperature of the solution to achieve an accurate conductivity measurement. Ordinarily, un-calibrated thermistors will have a variance of ±5% between their measured reading and the actual temperature. A calibrated thermistor may achieve a variance of ±1% or less.

In this regard, a sensor-specific Temperature Offset is calibrated at the factory. To determine the Temperature Offset, temperature readings are made while a 25.0° C. KCl solution is pumped through the fluid conduit and over the electrodes. A comparison is then made between the temperature reading of the un-calibrated thermistor on the sensor (Tsen) with that of a NIST-traceable thermometer or thermistor (Tref). The difference between the two readings is the Temperature Offset (Tref−Tsen=TempOffset). The Temperature Offset may have either a positive or a negative value. The sensor-specific Temperature Offset is then stored in the non-volatile memory on the sensor.

Each sensor has an "out-of-box" performance variance value which is also stored on the sensor, typically in the non-volatile memory chip. This "out-of-box" value is a statistically derived performance variance (measured in 0.100 molar KCl at 25.0° C.) that represents the maximum measurement error for that specific sensor within a 98% confidence limit. The statistically derived variance value is based on the performance analysis of all calibrated sensors within a production run, typically of between about 100 and about 500 sensor assemblies. The factory determined performance variance represents a predictive, "out-of-box" sensor performance level. This statistical treatment is analogous to and representative of a sensor validation procedure. Factory pre-validated conductivity sensors are thereby provided. The meaning of "pre-validated" is further illustrated herein, including as follows.

In the preferred embodiment, each conductivity sensor undergoes two factory measurements. The first measurement involves sensor calibration and determination of the specific Cell Constant (i.e. response factor) using a 0.100 molar KCl solution at 25.0° C. as described herein. In another separate and distinct measurement with 0.100 molar KCl solution at 25.0° C., the solution conductivity is experimentally determined using the pre-calibrated sensor. When taking into account the experimentally derived solution conductivities for all pre-calibrated sensors, the mean conductivity value closely centers around the theoretical value of 12,850 μS with a 3-sigma standard deviation of +/−190 μS or +/−1.5% An operator may access this information via the user interface 112 or Conductivity Monitor.

In addition to the calibration information, such as the Cell Constant (K) and the Temperature Offset, the sensor-specific Device ID, Calibration Date, and statistical information are store in the non-volatile memory. The Device ID is stored as a string of numbers, for example: nn-ss-xxxx-mmyy. In this example, the variables represent the sensor lot number (nn), fluid conduit size (ss), the device serial number (xxxx) and the manufacturing date by month and year (mmyy). For example, sensor containing the Device ID of 02-02-0122-1105 means that this sensor was the $122^{nd}$ sensor made in lot 02 of conduit size 02 (a fluid conduit with a diameter of ⅜" or 9.5 mm having a barb connector), manufactured in November of 2005. In this illustration, the sensor-specific Calibration Date or the date on which the sensor was calibrated using 0.100 molar KCl solution at 25.0° C. is also stored in the sensor's non-volatile memory as a separate data entry.

Additionally, statistical information or statistical data about the entire lot may also be stored in the non-volatile memory. For example, the average cell constant for lot 122 may be stored in the non-volatile memory of each sensor in lot 122. The standard deviation for cell constants for each lot may also be stored (i.e. "out-of-box" variance value) in the non-volatile memory of each sensor produced in that lot. This allows the user to determine whether a particular sensor is within the statistical range to achieve the proper margin of error for a specific experiment or bio-processing operation. As those skilled in the art will appreciate, other known statistical methods may be utilized, the results of which may be stored in the non-volatile memory on the sensing device.

In addition to storing the Cell Constant (K), Temperature Offset, Device ID, the Calibration Date, and other information in the non-volatile memory on the sensor, a summary of this information may be printed on the outside of the sensor. This information may be consulted by the user, used to later re-calibrate the sensor, and allows the user to input the printed information directly into the user interface.

It will be understood that the embodiments of the present invention which have been described are illustrative of some of the applications of the principles of the present invention. Numerous modifications may be made by those skilled in the art without departing from the true spirit and scope of the invention.

The invention claimed is:

1. A method of measuring the electrical conductivity of a bio-processing fluid, comprising:
   providing a particular pre-sterilized disposable electrical conductivity sensor assembly having a sensor component, a memory component and a conduit for directing a bio-processing fluid for electrical interaction with the bio-processing fluid flowing through the conduit;
   running a bio-processing fluid through the conduit of the particular electrical conductivity sensor assembly;
   passing a current through the particular electrical conductivity sensor component during said running of the bio-processing fluid through the conduit and measuring a resulting change in an electrical value across the sensor component, said change in electrical value being indicative of a measured electrical conductivity value of the bio-processing fluid;
   retrieving a sensor-specific constant stored on the memory component of the particular electrical conductivity sensor assembly; and
   calculating the actual electrical conductivity of the bio-processing fluid, said calculating comprising mathematically combining the measured electrical conductivity value with said stored constant.

2. The method according to claim 1, further including accounting for fluid temperature variance, comprising:
   measuring the temperature value of the bio-processing fluid running through the conduit for measuring its electrical conductivity;
   retrieving a temperature offset stored on the memory component of the electrical conductivity sensor assembly; and
   calculating the actual temperature of the bio-processing fluid, said calculating comprising mathematically combining the measured temperature value with said temperature offset.

3. The method according to claim 2, wherein said calculating of the actual electrical conductivity value comprises mathematically combining said calculated actual temperature with said measured electrical conductivity value and with said constant.

4. The method according to claim 1, wherein said mathematically combining includes multiplying the measured electrical conductivity value by said constant.

5. The method according to claim 2, wherein said mathematically combining includes dividing the measured electrical conductivity value by said constant.

6. The method according to claim 1, wherein said providing a memory component comprises providing a non-volatile memory chip.

7. The method according to claim 1, wherein said providing a memory component comprises providing a non-volatile memory chip that is an EEPROM.

* * * * *